(12) United States Patent
Yamazaki (10) Patent No.: US 6,908,280 B2
(45) Date of Patent: Jun. 21, 2005

(54) BLOOD PUMP

(75) Inventor: Kenji Yamazaki, Tokyo (JP)

(73) Assignee: Sun Medical Technology Research Corporation, Nagano (JP)

( * ) Notice: Subject to any disclaimer, the term of this patent is extended or adjusted under 35 U.S.C. 154(b) by 81 days.

(21) Appl. No.: 10/196,574

(22) Filed: Jul. 15, 2002

(65) Prior Publication Data

US 2003/0039544 A1 Feb. 27, 2003

(30) Foreign Application Priority Data

Aug. 10, 2001 (JP) ........................................ 2001-244277

(51) Int. Cl.$^7$ ................................................ F04D 7/02
(52) U.S. Cl. ...................................... 415/206; 415/900
(58) Field of Search ................................ 415/900, 206

(56) References Cited

U.S. PATENT DOCUMENTS

| | | | |
|---|---|---|---|
| 4,704,121 A | | 11/1987 | Moise |
| 4,898,518 A | * | 2/1990 | Hubbard et al. ............ 417/360 |
| 4,927,407 A | | 5/1990 | Dorman |
| 5,399,074 A | | 3/1995 | Nose et al. .............. 417/423.1 |
| 6,162,017 A | * | 12/2000 | Raible ........................ 415/206 |

* cited by examiner

Primary Examiner—Edward K. Look
Assistant Examiner—Dwayne J. White
(74) Attorney, Agent, or Firm—Hogan & Hartson, LLP (57) ABSTRACT

The blood pump of the present invention comprises:
- a first casing (1), its rim forming an opening;
- a second casing (2) having an inlet opening at the top and an outlet opening at an arbitrary position;
- a pump base part (5) attached to the first and second casings to partition them, its one side facing and covering the rim of the first casing, and the other side facing the base rim of the second casing;
- a drive part (7) housed inside the first casing driving a rotation shaft with a boss on the tip going roughly through the middle of the pump base part;
- a plurality of impellers (11) extending in radial direction from the outer periphery of the boss; and
- a pump part (3) constituted by the concurrence of the plurality of impellers and the second casing,
wherein the impellers' boss attachment parts are shifted forward towards the inlet opening.
wherein one part is cut out in each of the plurality of impellers' surfaces to form a window opening part (13).

As a result, the blood pump of the present invention ensures smooth blood flow and therefore allows to effectively prevent the development of thrombi.

20 Claims, 5 Drawing Sheets

BLOOD PUMP

BACKGROUND OF THE INVENTION

1. Field of the Invention

The present invention relates to a blood pump used for example in a ventricular assist device, and particularly relates to a blood pump having a construction that suppresses the development of thrombi.

2. Related Art

Axial flow, diagonal flow and centrifugal pumps are known as blood pumps for ventricular assist devices. As such a blood pump needs to be of a compact design in order to fit into the human body, its surface area needs to be large compared to its internal cubic capacity, and the clearance between the impellers and the casing needs to be large compared to the diameter. Therefore, substantial energy losses are incurred and the pump efficiency is considerably lower than that of ordinary larger pumps for industrial use.

Among the blood pumps stated above, centrifugal pumps are characterized by that the aspirated blood will hit perpendicularly upon the pump base part and will then be re-directed by centrifugal force in a right angle in the direction of the circumference. In this way, centrifugal pumps efficiently turn fluid motion energy into pressure energy by means of centrifugal force. Further, a hemolysis decrease can be expected due to the lower circumferential/angular velocity of centrifugal pumps as compared to axial pumps.

According to whether they feature a back plate (shroud), centrifugal pumps can be generally classified into open vane type, semi-open vane type and closed type centrifugal pumps.

Blood pumps are naturally restricted by the properties of blood. If blood stagnates, comes into contact with air or foreign bodies over a longer period of time, or is subjected to a higher temperature environment, it coagulates and thrombi form. Furthermore, the thrombi grow on these grounds. Blood properties like these form the reason for limitations regarding the blood pump construction.

The above-mentioned centrifugal pumps of the closed type or semi-open type feature a construction wherein the impellers are fitted to the back plate, and between the back plate and the pump base part the pump function does not take effect. Therefore, if closed type or semi-open type centrifugal pumps were used as a blood pump, the blood would stagnate at the backside of the back plate, leading to the development of thrombi. They are thus not appropriate as blood pumps.

Figure 7A:
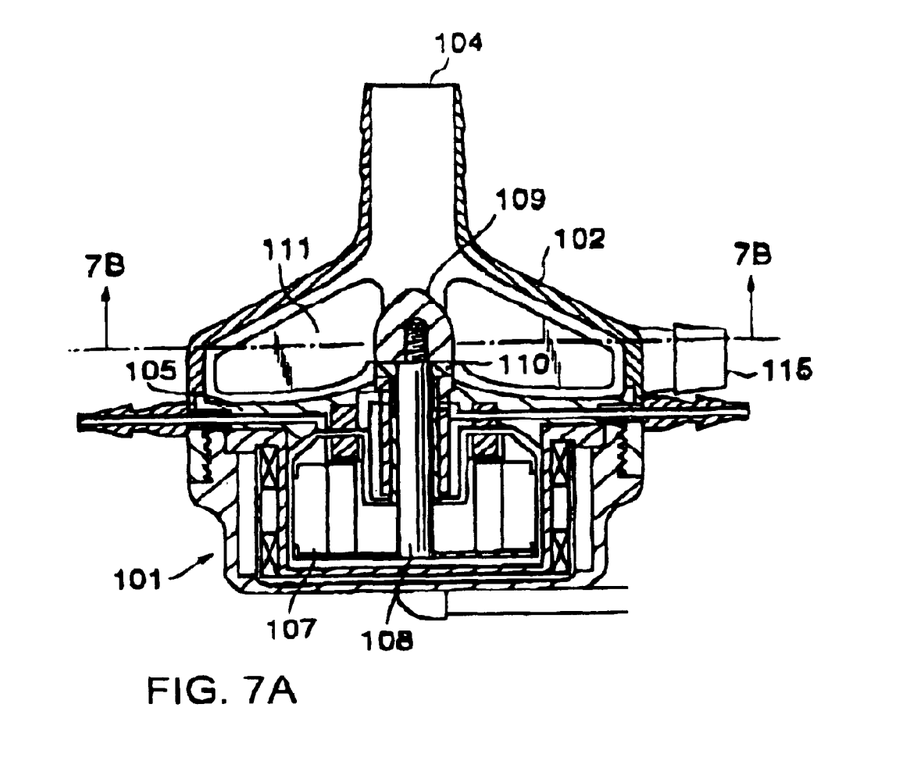
FIG. 7A is a longitudinal sectional view showing a conventional blood pump.

In contrast, open vane type centrifugal pumps as shown in FIG. 7A feature no back plate, the impellers being directly fitted to the rotation shaft tip, and therefore allow free flow of the blood in areas where thrombi have a tendency to develop in blood pump types featuring back plates.

Figure 7B:
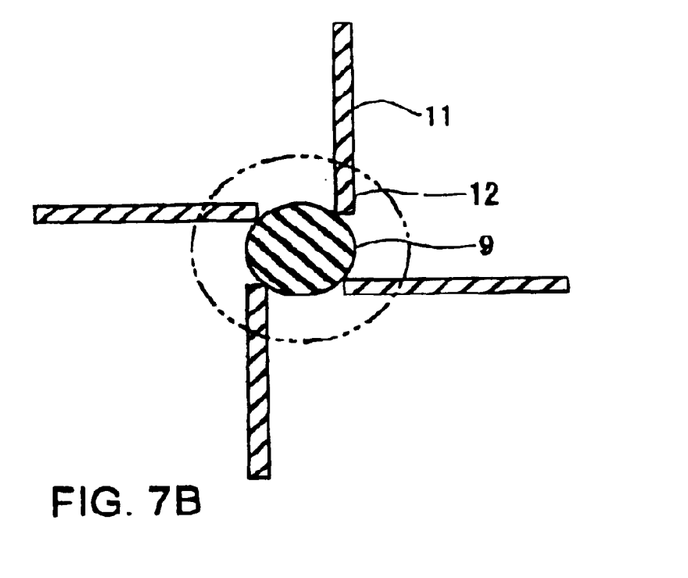
FIG. 7B is a transverse sectional view schematically showing the cross section 7B—7B of FIG. 7A.

Conventional blood pumps however, in order to yield a high pump efficiency, feature a construction wherein the impellers spread from the periphery of the boss in a uniform manner, and the blood flowing in the "vicinity of the periphery of the boss parts (boss, rotating side of the mechanical seal)" as exemplified by the inside of the chain double-dashed line of FIG. 7B is of a lower velocity than the blood in the radial outer areas and is of about the same velocity as the boss part.

Therefore, thrombi are likely to form inside the circle marked by the chain double-dashed line, as the blood is remaining in contact with parts that are foreign bodies to the blood (such as the boss and the impellers) over a longer period of time. When thrombi develop between the rotating part and the stationary part, the impeller rotation of the blood pump is obstructed. Furthermore, when the thrombi are scattered throughout the body, they end up clogging blood vessels. For example, when a thrombus reaches the brain it causes cerebral thrombosis.

Further, conventional blood pumps alter the blood current sharply, which is not necessarily desirable from a fluid dynamics point of view. According to conventional blood pumps, for example, the pump base part has a basically level surface on the pump part side, thus the blood is caused to stagnate and thrombi are likely to form.

In this way, the most important issue in blood pumps, as opposed to other fluid pumps, consists in solving the thrombus problem by all means.

It is the object of the present invention, in view of the above-mentioned circumstances, to provide a blood pump featuring a construction able to effectively prevent the development of thrombi.

SUMMARY OF THE INVENTION

The blood pump according to the present invention (first invention) comprises:

a first casing, its rim forming an opening;

a second casing having an inlet opening at the top and an outlet opening at an arbitrary position;

a pump base part attached to the first and second casings to partition them, its one side facing and covering the rim of the first casing, and the other side facing the base rim of the second casing;

a drive part housed inside the first casing driving a rotation shaft with a boss on the tip going roughly through the middle of the pump base part;

a plurality of impellers extending in radial direction from the outer periphery of the boss; and a pump part constituted by the concurrence of the plurality of impellers and the second casing, wherein the impellers' boss attachment parts are shifted forward towards the inlet opening.

Conventionally, the impellers' boss attachment parts are placed at the widened part of the second casing, and therefore as they are exposed to blood flow that has slowed down with the widening of the second casing, thrombi are likely to form at the impeller's boss attachment parts as a result. According to the present invention (first invention) however, these impellers' boss attachment parts are shifted forward towards the inlet opening, and therefore the development of thrombi is effectively suppressed at the impellers' boss attachment parts, as they are exposed to blood flow that is faster than where the second casing is considerably widening.

Further, according to the present invention (first invention), due to shifting forward the boss attachment parts towards the inlet opening, it is possible to display the function of the impellers' enhanced sucking properties as an inducer.

According to a further preferred embodiment of the present invention (first invention), the impeller's boss attachment parts are shifted forward up to the axial flow zone where the blood mainly flows in the direction along the rotation shaft.

Therefore, the impeller's boss attachment parts are exposed to sufficiently fast blood flow, and as a result, the development of thrombi is furthermore effectively suppressed at the impellers' boss attachment parts.

According to a preferred embodiment of the present invention (first invention), one part is cut out in each of the plurality of impellers' surfaces to form a window opening (recess or clearance) part, which is located downstream from the impellers' boss attachment part on the impellers' rotation shaft side.

Therefore, according to the blood pump of the present invention (first invention), the relative velocity between the boss part (boss and rotating part of the mechanical seal) and the blood flowing in the boss part periphery is increased due to the window opening part, thereby furthermore effectively preventing the development of thrombi.

According to a further preferred embodiment of the present invention (first invention), a mechanical seal is provided at the base rim side of the boss of about the same diameter as the boss base rim, the window opening part is cut out starting from the position where the impellers are supported by the boss and continuing so as to avoid the rotating part of the mechanical seal, with the end of the cut out line being formed to correspond to the position of the friction surface of the mechanical seal.

Figure 4:
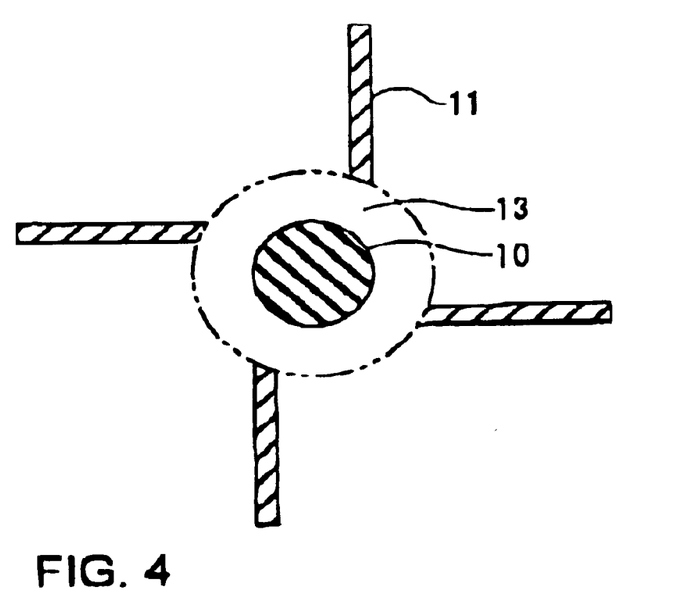
FIG. 4 is a cross-sectional view schematically showing a transverse sectional view of the impellers and the mechanical seal along the 4—4 cut-line of the window opening part, for the case that the blood pump of the present invention has 4 impellers.

FIG. 4 is a cross-sectional view schematically showing a side cross-section of the impellers and the boss or mechanical seal respectively along the 4—4 cut-line of the window opening part (of FIG. 2), for the case that the blood pump of the present invention has 4 impellers. In this cross-section, inside the chain double-dashed line circle the blood is allowed to pass through the window opening part, resulting in a high relative velocity between the (rotating) part of the mechanical seal figured in FIG. 4 by the center circle that is rotating, and the slowly flowing blood inside the chain double-dashed line circle.

Figure 5:
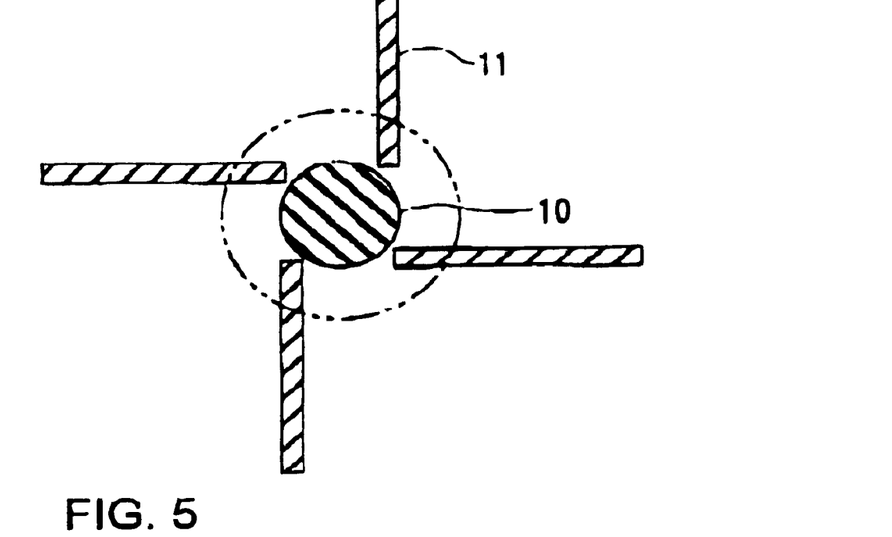
FIG. 5 is a cross-sectional view schematically showing a side transverse sectional view of the impellers and the pump base part along the 5—5 cut-line of the mechanical seal's friction surface, for the case that the blood pump of the present invention has 4 impellers.

FIG. 5 is a cross-sectional view schematically showing a side cross-section of the impellers and the mechanical seal along the 5—5 cut-line of the mechanical seal's friction surface (of FIG. 2), for the case that the blood pump of the present invention has 4 impellers. In this cross-section, the impeller's inner outline is drawn close to the boss part again. Inside the chain double-dashed line circle motion energy is applied to the blood by the impellers, resulting in a high relative velocity between the stationary part of the mechanical seal (pump base part) figured in FIG. 5 by the center circle that is not rotating, and the rapidly flowing blood inside the chain double-dashed line circle.

Therefore, the blood does not stagnate in the periphery of the boss part and the forming of thrombi at the boss part or impeller surfaces in contact with blood is suppressed.

According to a preferred embodiment of the present invention (first invention), the inner wall of the second casing is tapered, continuously increasing in width from the inlet opening towards the base rim, and formed to draw as close as possible to the outer outline of the impellers, the boss and impellers being surrounded by the inner wall and protruding towards the inlet opening.

In this case, the inlet opening works as a diffuser of the widening flow paths changing one part of the velocity head to a pressure head, and the blood is aspirated inside the second casing while avoiding any sudden change in the cross-sectional area of the flow paths. And, as the boss part and impellers are drawn close to and protruding towards the inlet opening, the blood is sent to the pump part while keeping its high velocity. In this way, the forming of thrombi is furthermore effectively prevented.

According to a further preferred embodiment of the present invention (first invention), the clearance between the second casing's inner wall and the impellers' outer outline is 0.1 mm or above and 3.0 mm or below. By reducing the clearance to 3.0 mm or below, sufficient pump function is effectuated also in the vicinity of the second casing's inner wall. From this point of view, a clearance of 2.0 mm or below is more preferable, and a clearance of 1.2 mm or below is even more preferable.

Furthermore, by increasing the clearance to 0.1 mm or above it is prevented that the impeller's outer outline collides with the second casing's inner wall, even if the rotation shaft is slightly off its center axis due to the pump's vibration or the like. From this point of view, a clearance of 0.2 mm or above is more preferable, and a clearance of 0.3 mm or above is even more preferable.

According to a further preferred embodiment of the present invention (first invention), each impeller of the plurality of impellers features an inducer on the inlet opening side of the impeller, the inducer being layed-out to be inclined at a prescribed angle against each impeller.

Figure 2:
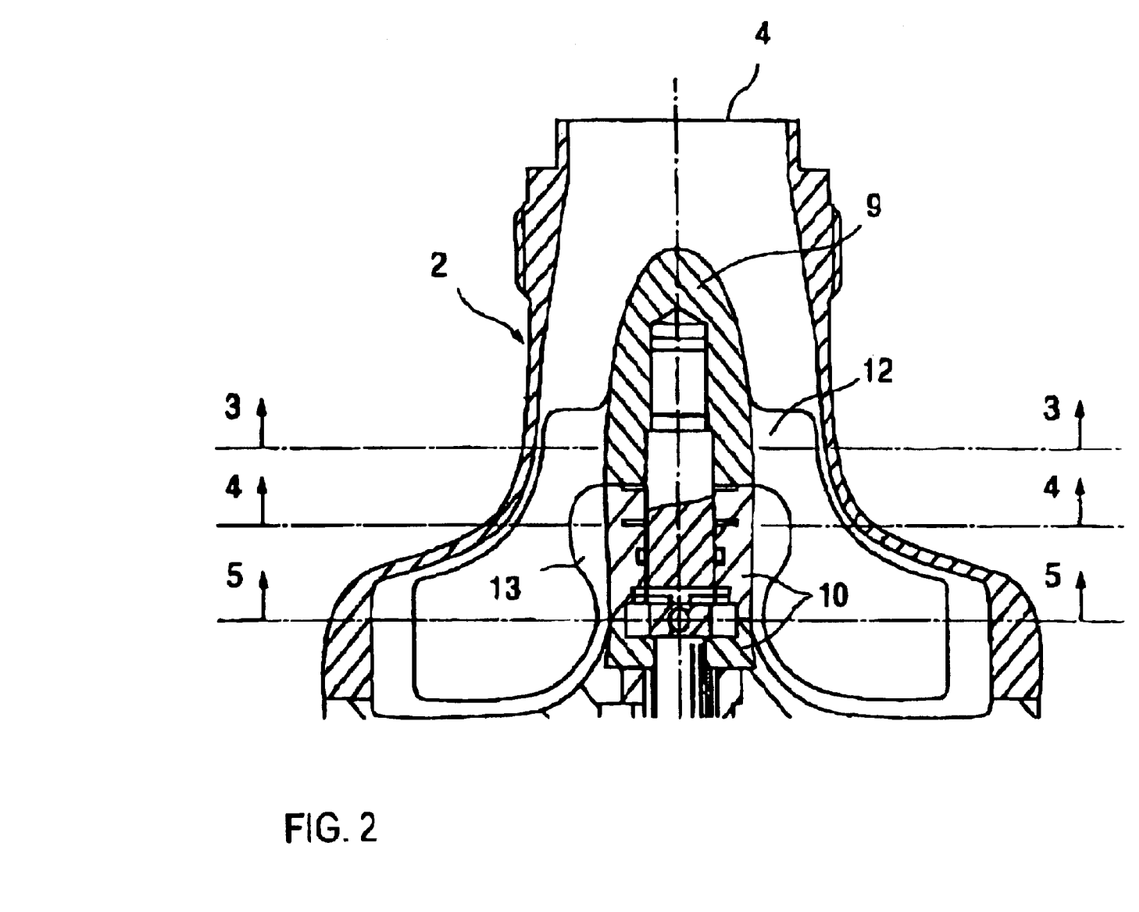
FIG. 2 is an enlarged view showing the pump part of the blood pump of FIG. 1.
Figure 3:
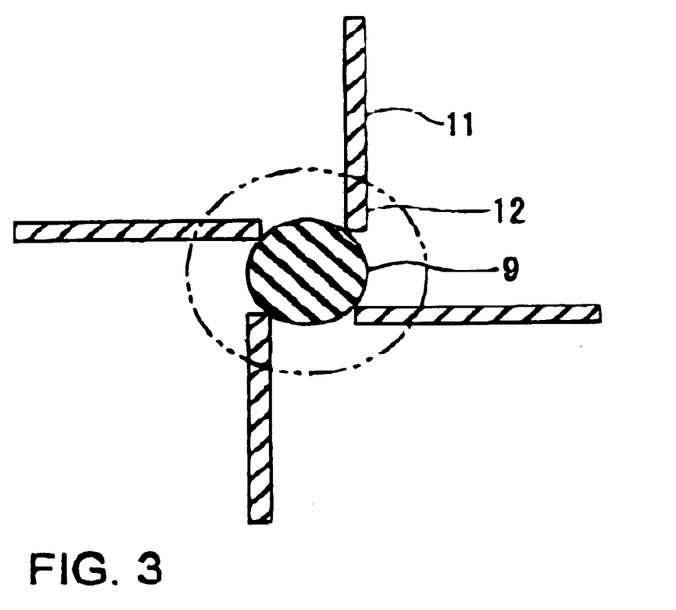
FIG. 3 is a cross-sectional view schematically showing a transverse sectional view of the boss and the impellers along the 3—3 cut-line of the impellers' support part, for the case that the blood pump of the present invention has 4 impellers.

FIG. 3 is a cross-sectional view schematically showing a side cross-section of the boss and the impellers and the support part along the 3—3 cut-line of the impellers' support part (of FIG. 2), for the case that the blood pump of the present invention has 4 impellers.

As shown in this figure, in the side cross-section of the boss' impeller support, equal to the impeller in parts with no window opening part, the blood inside the chain double-dashed line circle is rotated at about the same rotation velocity as the boss or mechanical seal or also the impellers, resulting in very little relative velocity in relation to them.

However, the construction of the present invention, together with shifting the impellers' boss attachment parts forward towards the inlet opening, provides inducers to enhance the aspiration effect of the impellers. By forcing the blood flow from the inlet opening to the window opening part, the blood is not allowed to settle in the vicinity of the impeller support parts, as the blood is sent in a continuous flow from the inlet opening to the window opening parts below.

Therefore, in the periphery of the boss in the vicinity of the impeller support parts the blood does not stagnate, and the forming of thrombi is thus suppressed. Furthermore, through this inducer the blood is aspirated while keeping a fluid dynamically natural flow. Hemolysis can thus be prevented, or at least reduced, as the shocks inside the flow, and sudden changes of flow are suppressed.

According to a further preferred embodiment of the present invention (first invention), the pump base part features a convex part protruding towards the second casing, the convex part's flank being formed to slope gently so as to draw as close as possible to the inner outline of the impellers.

In embodiments like this, a natural blood flow without any sudden flow path changes of the blood is effectuated in the pump part. And, as the impellers and the pump base part are formed so as to draw as close as possible as shown in FIG. 5, the pump function works even at the pump base part surface.

Therefore, the blood is made to flow efficiently, and the problem of blood stagnation due to the construction is naturally resolved.

According to a further preferred embodiment of the present invention (first invention), the clearance between the pump base part and the inner outline of the impellers ranges between 0.05 mm and 3.0 mm.

By reducing the clearance to 3.0 mm or below, sufficient pump function is effectuated also at the surface of the pump base part. From this point of view, a clearance of 2.0 mm or below is more preferable, and a clearance of 1.2 mm or below is even more preferable.

Furthermore, by increasing the clearance to 0.05 mm or above, it is avoided that the impeller's inner outline collides with the pump base part, even if the mechanical seal's friction surface is worn by abrasion with long term usage. From this point of view, a clearance of 0.1 mm or above is more preferable, and a clearance of 0.2 mm or above is even more preferable.

According to a further preferred embodiment of the present invention (first invention), one part is cut out in each of the plurality of impellers' surfaces to form a window opening part;

the inner wall of the second casing is tapered, continuously increasing in width from the inlet opening towards the base rim, and is formed to draw as close as possible to the outer outline of the impellers, the boss and impellers being surrounded by the inner wall and protruding towards the inlet opening;

each impeller of the plurality of impellers features an inducer on the inlet opening side of the impeller, the inducer being layed-out to be inclined at a prescribed angle against each impeller; and the pump base part features a convex part protruding towards the second casing, the convex part's flank being formed to slope gently so as to draw as close as possible to the inner outline of the impellers.

Therefore, according to this embodiment, the blood flow as a whole becomes smoother, and the development of thrombi is further effectively prevented.

The blood pump according to the present invention (second invention) comprises:

a first casing, its rim forming an opening;

a second casing having an inlet opening at the top and an outlet opening at an arbitrary position;

a pump base part attached to the first and second casings to partition them, its one side facing and covering the rim of the first casing, and the other side facing the base rim of the second casing;

a drive part housed inside the first casing driving a rotation shaft with a boss on the tip going roughly through the middle of the pump base part;

a plurality of impellers extending in radial direction from the outer periphery of the boss; and a pump part constituted by the concurrence of the plurality of impellers and the second casing, wherein one part is cut out in each of the plurality of impellers' surfaces to form a window opening part.

Therefore, according to the blood pump of the present invention (second invention), the relative velocity between the boss part (boss and rotating part of the mechanical seal) and the blood flowing in the boss part periphery is increased due to the window opening part, thereby furthermore effectively preventing the development of thrombi.

According to a preferred embodiment of the present invention (second invention), a mechanical seal is provided at the base rim side of the boss of about the same diameter as the boss base rim, the window opening part is cut out starting from the position where the impellers are supported by the boss and continuing so as to avoid the rotating part of the mechanical seal, with the end of the cut out line being formed to correspond to the position of the friction surface of the mechanical seal.

Therefore, the blood does not stagnate in the periphery of the boss part, and the forming of thrombi is suppressed at the surface of the impeller and boss part in contact with blood.

The blood pump according to the present invention (third invention) comprises:

a first casing, its rim forming an opening;

a second casing having an inlet opening at the top and an outlet opening at an arbitrary position;

a pump base part attached to the first and second casings to partition them, its one side facing and covering the rim of the first casing, and the other side facing the base rim of the second casing;

a drive part housed inside the first casing driving a rotation shaft with a boss on the tip going roughly through the middle of the pump base part;

a plurality of impellers extending in radial direction from the outer periphery of the boss; and a pump part constituted by the concurrence of the plurality of impellers and the second casing, wherein the inner wall of the second casing is tapered, continuously increasing in width from the inlet opening towards the base rim, and formed to draw as close as possible to the outer outline of the impellers, the boss and impellers being surrounded by the inner wall and protruding towards the inlet opening.

Therefore, according the present invention (third invention), the inlet opening works as a diffuser of the widening flow paths changing one part of the velocity head to a pressure head, the blood is aspirated inside the second casing while avoiding any sudden change in the cross-sectional area of the flow paths. And, as the boss part and impellers are drawn close to and protruding towards the inlet opening, the blood is sent to the pump part while keeping its high velocity.

Therefore, the forming of thrombi is effectively prevented.

According to a preferred embodiment of the present invention (third invention), the clearance between the second casing's inner wall and the impellers' outer outline ranges between 0.1 mm and 3.0 mm.

By reducing the clearance to 3.0 mm or below, sufficient pump function is effectuated also in the vicinity of the second casing's inner wall. From this point of view, a clearance of 2.0 mm or below is more preferable, and a clearance of 1.2 mm or below is even more preferable.

Furthermore, by increasing the clearance to 0.1 mm or above it is prevented that the impeller's outer outline collides with the second casing's inner wall, even if the rotation shaft is slightly off its center axis due to the pump's vibration or the like. From this point of view, a clearance of 0.2 mm or above is more preferable, and a clearance of 0.3 mm or above is even more preferable.

The blood pump according to the present invention (fourth invention) comprises:

a first casing, its rim forming an opening;

a second casing having an inlet opening at the top and an outlet opening at an arbitrary position;

a pump base part attached to the first and second casings to partition them, its one side facing and covering the rim of the first casing, and the other side facing the base rim of the second casing;

a drive part housed inside the first casing driving a rotation shaft with a boss on the tip going roughly through the middle of the pump base part;

a plurality of impellers extending in radial direction from the outer periphery of the boss; and a pump part constituted by the concurrence of the plurality of impellers and the second casing, wherein each impeller of the plurality of impellers features an inducer on the inlet opening side of the impeller, the inducer being layed-out to be inclined at a prescribed angle against each impeller.

Preferably, the inducers are shifted forward towards the inlet opening.

Therefore, according to the blood pump of the present invention (fourth invention), as described above, the blood does not settle in the vicinity of the support part of the impeller, and is expedited from the inlet opening in a continuous flow down to the window opening part.

Therefore, in the periphery of the boss in the vicinity of the impeller support parts the blood does not stagnate, and the forming of thrombi is thus suppressed. Furthermore, by this inducer the blood is aspirated while keeping a fluid dynamically natural flow. Hemolysis can thus be prevented, or at least reduced, as the shocks inside the flow, and sudden changes of flow are suppressed.

The blood pump according to the present invention (fifth invention) comprises:

a first casing, its rim forming an opening;

a second casing having an inlet opening at the top and an outlet opening at an arbitrary position;

a pump base part attached to the first and second casings to partition them, its one side facing and covering the rim of the first casing, and the other side facing the base rim of the second casing;

a drive part housed inside the first casing driving a rotation shaft with a boss on the tip going roughly through the middle of the pump base part;

a plurality of impellers extending in radial direction from the outer periphery of the boss; and a pump part constituted by the concurrence of the plurality of impellers and the second casing, wherein the pump base part features a convex part protruding towards the second casing, the convex part's flank being formed to slope gently so as to draw as close as possible to the inner outline of the impellers.

Therefore, according to the present invention (fifth invention), a natural blood flow without any sudden flow path changes of the blood is effectuated in the pump part. And, as the impellers and the pump base part are formed so as to draw as close as possible as shown in FIG. 5, the pump function works even at the pump base part surface.

Therefore, the blood is made to flow efficiently, and the problem of blood stagnation due to the construction is naturally resolved.

A blood pump according to claim 16, wherein the clearance between the pump base part and the inner outline of the impellers ranges between 0.05 mm and 3.0 mm.

By reducing the clearance to 3.0 mm or below, sufficient pump function is effectuated also at the surface of the pump base part. From this point of view, a clearance of 2.0 mm or below is more preferable, and a clearance of 1.2 mm or below is even more preferable.

Furthermore, by increasing the clearance to 0.05 mm or above, it is avoided that the impeller's inner outline collides with the pump base part, even if the mechanical seal's friction surface is worn by abrasion with long term usage. From this point of view, a clearance of 0.1 mm or above is more preferable, and a clearance of 0.2 mm or above is even more preferable.

Finally, in the blood pump according to the present invention, the degree to which the impellers' boss attachment parts is shifted forward, the shape of the window opening part, the shape of the inner wall of the second casing, the degree to which the convex part of the pump base part inclines, the shape of the inducers attached to the impellers and the like, are not limited as long as the blood flow becomes smoother within the scope of the claims or technical ideas of the present invention.

DETAILED DESCRIPTION OF PREFERRED EMBODIMENTS

Figure 1:
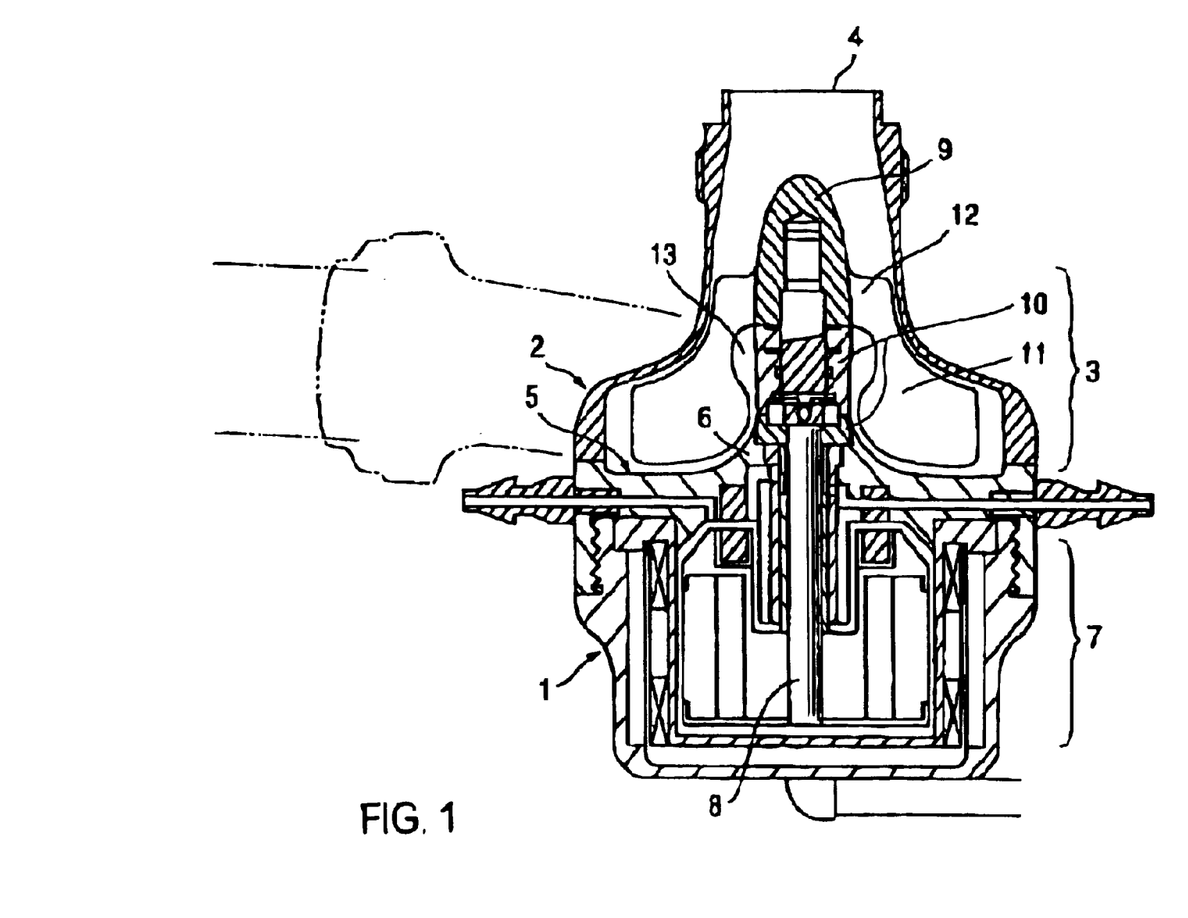
FIG. 1 is a longitudinal sectional view of the blood pump according to one embodiment of the present invention.

The blood pump according to the present invention will now be explained in detail with reference to FIG. 1, which shows a cross-sectional view of a blood pump according to a preferred embodiment of the present invention. Throughout the Figures, Numeral 1 refers to the cylindrical first casing, having a rim forming an opening, Numeral 2 refers to the second casing which houses pump part 3 that will be explained later. This second casing 2 provides a blood suction inlet opening 4 at its top rim, and on its periphery an outlet opening for the expulsion of blood by the pump (shown only schematically in FIG. 1 by the chain double-dashed line). The inner wall of the second casing 2 is tapered, continuously increasing in width from the inlet opening 4 towards the base rim. This second casing 2 may be of a transparent material to allow the observation and confirmation of the blood's color and condition.

Numeral 5 refers to a pump base part that is attached for example by screwing to the first and second casings to partition them, its one side facing and covering the rim of the first casing, and the other side facing the base rim of the second casing. This pump base part 5 is of a disk-like shape having a cone shaped convex part about in the middle on the side of the second casing 2. The flank of this convex part 5 slopes gently, and preferably is curved concavely towards the middle.

A drive part 7 is housed inside the first casing 1 driving (for example by a motor or the like) a rotation shaft 8, that goes through the middle of the convex part 6 of the pump base part 2, surpassing it up to the pump part 3, and features a boss 9 at the tip.

Between the top rim of the convex part 6 and the base rim of the boss 9, the rotating side of a mechanical seal 10 is provided to prevent the inflow of blood towards the inside of the bearing of the rotation shaft 8. The stationary part of this mechanical seal is formed in accordance with the slope of the flank of the convex part 6 to provide a smooth connection. Further, this mechanical seal 10 is formed so that its friction surface is positioned to coincide with the top rim of the convex part 6. The respective cross-section areas of the base rim of the boss and the mechanical seal on the rotating side, and the top rim of the convex part 6 are formed as concentric circles of about equal diameters.

The boss 9 is surrounded by the of the second casing 2, and while the base rim of the boss 9 is attached to the upper side of the mechanical seal, rotating with the rotating side of the mechanical seal, the tip of the boss 9 protrudes towards the inlet opening 4 of the second casing 2. Further, in order to allow the blood aspirated from the inlet opening 4 to flow naturally, the boss 9 is formed to be of a fluid-dynamically preferable parabolic shape seen in the longitudinal cross-section.

Compared to conventional boss attachment parts, the boss attachment parts of the impellers 11 have been shifted forward towards the inlet opening 4. Therefore, these boss attachment parts are exposed to the blood flow in an area of axial flow before the second casing 2 widens to any degree of importance. Extending in radial direction from the outer periphery of this boss 9, a plurality of impellers 11 evenly spaced around the periphery are supported by the support parts 12. These support parts 12 of the impellers, together with the boss 9, are provided in an area close to the inlet opening 4, in order to be able to send the blood aspirated from the inlet opening 4 of the second casing 2 to the pump part 3, while keeping the blood's high flow velocity.

In each impeller 11, as shown in FIG. 2, a window opening (recess or clearance) part 13 is cut out to avoid the periphery of the rotating part of the mechanical seal 10, when the impellers 11 rotate. This window opening part 13 is formed so that this inner outline draws close to the base rim of the boss 9, that is to say, from the lower side of the support part 12 of the impeller to the vicinity of the convex part 6 of the pump base part 5, with the end of the cut out line being formed to correspond to the position of the friction surface of the mechanical seal.

The pump part 3 is constituted by the concurrence of the boss 9, the impellers 11 and the second casing 2.

And, the inner outline of the impellers 11 is drawn as close as possible to the pump base part 5 (including the convex part) starting from the position of the friction surface of the mechanical seal, that is to say, the end of the cut out, and the outer outline of the impellers 11 is drawn as close as possible to the tapered inner wall of the second casing 2 from the support part 12, each extending towards the periphery of the pump part 3.

The clearance between the pump base part 5 and the inner outline of the impeller 11 being 0.8 mm, this allows sufficient pump effect to work even on the surface of the pump base part and at the same time allows to avoid the collision of the impellers' inner outline with the pump base part due to wear at the friction surface of the mechanical seal that comes with long term operation.

Further, the clearance between the inner wall of the second casing 2 and the outer outline of the impellers being 0.7 mm, this allows sufficient pump effect to work even in the vicinity of the inner wall of the second casing and at the same time allows to avoid the collision of the impellers' outer outline with the inner wall of the second casing for excentricities of the rotation shaft due to vibrations of the pump and the like.

Figure 6:
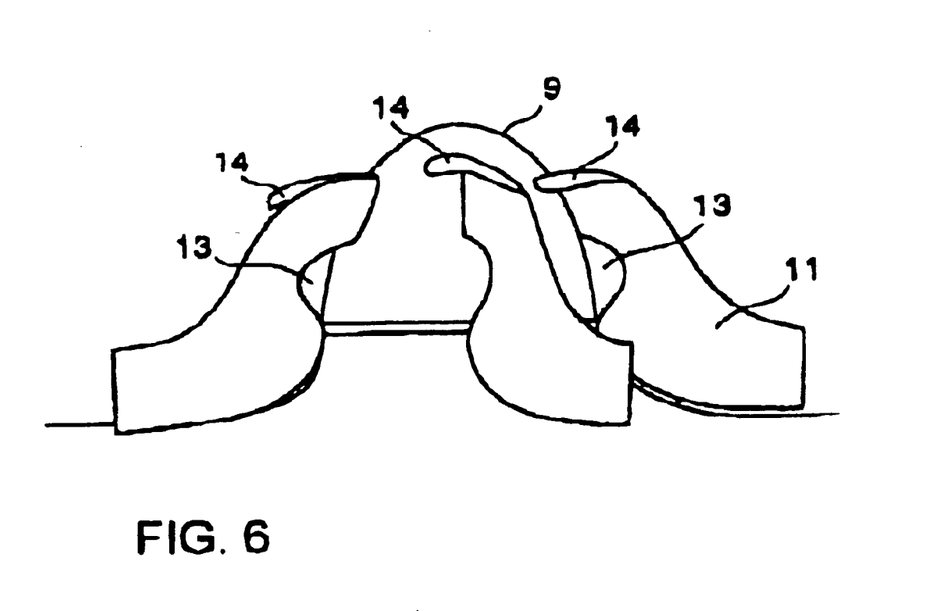
FIG. 6 is a front view schematically showing the inducers provided at the impellers.

FIG. 6 is a front view schematically showing an impeller provided with an inducer 14 according to a preferable embodiment of the present invention. These inducers 14 are provided of each of the support parts 12 of the plurality of impellers 11 on the inlet opening side 4. Each inducer 14 is inclined at a predetermined angle towards the surface of the impeller 11. Preferably, it is located close to the inlet opening 4, together with the boss 9 and the support part 12 of the impeller 11.

The blood aspirated from the inlet opening 4, is sent to the blood pump without any sudden changes in the cross-sectional area of the flow paths, with the inner wall of the second casing 2 being tapered, widening from the inlet opening 4 towards the base rim, working as a diffuser 14. And, due to the fluid-dynamically desirable tip form of the boss 9, it is sent to the support part 12 of the impeller 11, while keeping its natural way of flowing.

At this point, it is preferable for the blood to be forced to flow downwards to the window opening by the inducer. Thereby, it is assured that the blood does not accumulate between the impellers 11 and their support parts 12 in the periphery of the boss support part 12 shown in FIG. 3.

One part of the blood made to flow into the area of the window opening 13 is directed towards the periphery by the impellers 11, the other part of the blood reaches the window opening part 13. Because its relative velocity to the rotating part of the mechanical seal 10 is high, the blood reaching the window opening part 13 is sent further downward without accumulating.

Finally, at the bottom of the pump base part, the velocity and pressure of the blood are increased through the centrifugal pump and the blood is then expulsed through the outlet opening provided at the circumference. At this point, as the inner outline of the impeller 11 and the surface of the pump base part 5 are constructed so as to be drawn as close as possible to each other, the impellers 11 of the pump cause a wash-out effect on the blood at the surface of the pump base part 5 that leads the blood to be forced out without accumulating.

Furthermore, the pump base part 5 brings about a natural flow of blood, as it features a convex part 6 that has been raised to a cone-shape, and the flank of this convex part 6 is curved on the side of the rotation shaft 8.

As described above, the blood pump according to the present invention allows to convert the aspirated flow of blood to smoothly proceed towards the periphery, due to the fluid-dynamically desirable construction for all blood flow paths, and thus allows the effective suppression of the forming of thrombi without any accumulation of the blood.

In FIG. 7, the reference numerals of the present invention to which 100 has been added correspond to the reference numerals in the conventional example.

What is claimed is:

1. A blood pump, comprising:

a first casing, its rim forming an opening;

a second casing having an inlet opening at the top and an outlet opening at an arbitrary position;

a pump base part attached to the first and second casings to partition them, its one side facing and covering the rim of the first casing, and the other side facing the base rim of the second casing;

a drive part housed inside the first casing driving a rotation shaft with a boss on the tip going roughly through the middle of the pump base part;

a plurality of impellers extending in radial direction from the outer periphery of the boss; and a pump part constituted by the concurrence of the plurality of impellers and the second casing, wherein one part is cut out in each of the plurality of impellers' surfaces to form a window opening part, which is located downstream from the impellers' boss attachment part.

2. A blood pump according to claim 1, wherein a mechanical seal is provided at the base rim side of the boss of about the same diameter as the boss base rim, the window opening part is cut out starting from the position where the impellers are supported by the boss and continuing so as to avoid the rotating part of the mechanical seal, with the end of the cut out line being formed to correspond to the position of the friction surface of the mechanical seal.

3. The blood pump according to claim 1, wherein the pump base part features a convex part protruding towards the second casing, the convex part's flank being formed to slope gently so as to draw as close as possible to the inner outline of the impellers.

4. The blood pump according to claim 1, wherein the impellers' boss attachment parts are shifted up to the axial flow zone towards the inlet opening.

5. The blood pump according to claim 1, wherein the inner wall of the second casing is tapered, continuously increasing in width from the inlet opening towards the base rim, and formed to draw as close as possible to the outer outline of the impellers, the boss and impellers being surrounded by the inner wall and protruding towards the inlet opening.

6. The blood pump according to claim 5, wherein the clearance between the second casings' inner wall and the impellers' outer outline ranges between 0.1 mm and 3.0 mm.

7. The blood pump according to claim 1, wherein each impeller of the plurality of impellers features an inducer on the inlet opening side of the impeller, the inducer being layed-out to be inclined at a prescribed angle against each impeller.

8. The blood pump according to claim 7, wherein the clearance between the pump base part and the inner outline of the impellers ranges between 0.05 mm and 3.0 mm.

9. The blood pump according to claim 7, wherein the clearance between the convex part's flank of the pump base part and the inner outline of the impellers keeps almost the same distance from inner to outer.

10. A blood pump, comprising:

a first casing, its rim forming an opening;

a second casing having an inlet opening at the top and an outlet opening at an arbitrary position;

a pump base part attached to the first and second casings to partition them, its one side facing and covering the rim of the first casing, and the other side facing the base rim of the second casing;

a drive part housed inside the first casing driving a rotation shaft with a boss on the tip going roughly through the middle of the pump base part;

a plurality of impellers extending in radial direction from the outer periphery of the boss; and a pump part constituted by the concurrence of the plurality of impellers and the second casing, wherein each impeller of the plurality of impellers features an inducer on the inlet opening side of the impeller, the inducer being layed-out to be inclined at a prescribed angle against each impeller.

11. A blood pump according to claim 10, wherein the inducers are shifted forward towards the inlet opening.

12. The blood pump according to claim 10, wherein the impellers' boss attachment parts are shifted up to the axial flow zone towards the inlet opening.

13. The blood pump according to claim 10, wherein a mechanical seal is provided at the base rim side of the boss of about the same diameter as the boss base rim, the window opening part is cut out starting from the position where the impellers are supported by the boss and continuing so as to avoid the rotating part of the mechanical seal, with the end of the cut out line being formed to correspond to the position of the friction surface of the mechanical seal.

14. The blood pump according to claim 10, wherein the inner wall of the second casing is tapered, continuously increasing in width from the inlet opening towards the base rim, and formed to draw as close as possible to the outer outline of the impellers, the boss and impellers being surrounded by the inner wall and protruding towards the inlet opening.

15. The blood pump according to claim 14, wherein the clearance between the second casing's inner wall and the impellers' outer outline ranges between 0.1 mm and 3.0 mm.

16. The blood pump according to claim 10, wherein the pump base part features a convex part protruding towards the second casing, the convex part's flank being formed to slope gently so as to draw as close as possible to the inner outline of the impellers.

17. The blood pump according to claim 16, wherein the clearance between the pump base part and the inner outline of the impellers ranges between 0.05 mm and 3.0 mm.

18. The blood pump according to claim 16, wherein the clearance between the convex part's flank of the pump base part and the inner outline of the impellers keeps almost the same distance from inner to outer.

19. A blood pump comprising:

a first casing, its rim forming an opening:

a second casing having an inlet opening at the top and an outlet opening at an arbitrary position;

a pump base part attached to the first and second casings to partition them, its one side facing and covering the rim of the first casing, and the other side facing the base rim of the second casing;

a drive part housed inside the first casing driving a rotation shaft with a boss on the tip going roughly through the middle of the pump base part; a plurality of impellers extending in a radial direction from the outer periphery of the boss; and a pump part constituted by the concurrence of the plurality of impellers and the second casing, wherein the impellers' boss attachment parts are shifted up to the axial flow zone forward towards the inlet opening, and wherein each impeller of the plurality of impellers features an inducer on the inlet opening side of the impeller, the inducer being layed-out to be inclined at a prescribed angle against each impeller.

20. A blood pump comprising:

a first casing, its rim forming an opening;

a second casing having an inlet opening at the top and an outlet opening at an arbitrary position;

a pump base part attached to the first and second casings to partition them, its one side facing and covering the rim of the first casing, and the other side facing the base rim of the second casing;

a drive part housed inside the first casing driving a rotation shaft with a boss on the tip going roughly through the middle of the pump base part; a plurality of impellers extending in a radial direction from the outer periphery of the boss; and a pump part constituted by the concurrence of the plurality of impellers and the second casing, wherein the impellers' boss attachment parts are shifted up to the axial flow zone forward towards the inlet opening, and wherein one part is cut out in each of the plurality of impellers' surfaces to form a window opening part;

the inner wall of the second casing is tapered, continuously increasing in width from the inlet opening towards the base rim, and is formed to draw as close as possible to the outer outline of the impellers, the boss and impellers being surrounded by the inner wall and protruding towards the inlet opening;

each impeller of the plurality of impellers features an inducer on the inlet opening side of the impeller, the inducer being layed-out to be inclined at a prescribed angle against each impeller; and the pump base part features a convex part protruding towards the second casing, the convex part's flank being formed to slope gently so as to draw as close as possible to the inner outline of the impellers.

* * * * *